United States Patent
Nakamura et al.

(10) Patent No.: US 6,686,413 B2
(45) Date of Patent: Feb. 3, 2004

(54) CYCLOHEXYLALKYL (METH) ACRYLATE ESTER-BASED RESIN COMPOSITION

(75) Inventors: Kazuhiko Nakamura, Kawanishi (JP); Yoshiyuki Yokota, Suita (JP); Kunio Takahashi, Takatsuki (JP); Masaya Yoshida, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 176 days.

(21) Appl. No.: 09/938,653

(22) Filed: Aug. 27, 2001

(65) Prior Publication Data
US 2002/0045702 A1 Apr. 18, 2002

(30) Foreign Application Priority Data
Aug. 30, 2000 (JP) ........................................ 2000-261763

(51) Int. Cl.$^7$ ....................... C08F 220/18; C09D 133/06
(52) U.S. Cl. ........................................ 524/553; 526/308
(58) Field of Search ........................... 524/553; 526/308

(56) References Cited

U.S. PATENT DOCUMENTS

| 4,594,448 A | 6/1986 | Hohage ....................... 560/220 |
| 5,239,028 A | 8/1993 | Nakagawa et al. ......... 526/265 |
| 5,492,944 A | * 2/1996 | Elser et al. ................. 523/201 |
| 5,534,579 A | 7/1996 | Nikaya et al. .............. 524/460 |

FOREIGN PATENT DOCUMENTS

| JP | 5413544 | 2/1979 | |
| JP | 54013544 A | * 2/1979 | .............. C09J/3/14 |
| JP | 3128978 | 5/1991 | |
| JP | 5140240 | 6/1993 | |
| JP | 6122734 | 5/1994 | |
| JP | 06122734 A | * 5/1994 | ......... C08F/220/18 |
| JP | 6313088 | 11/1994 | |
| JP | 06313088 A | * 11/1994 | ........... C08L/33/08 |

* cited by examiner

*Primary Examiner*—Kelechi C. Egwim
(74) *Attorney, Agent, or Firm*—Roylance, Abrams, Berdo & Goodman, L.L.P.

(57) ABSTRACT

The present invention provides a novel (meth)acrylate ester-based resin composition which, for example, exhibits various good properties such as weather resistance, heat resistance, water resistance, acid resistance, alkali resistance, warm water resistance, impact resistance, flexibility, processability, adhesion, hardness, and elongation when being used for various uses such as coating agents (e.g. for films, plastics, glass, paper, fibers, leather), pressure sensitive adhesives, and adhesives in addition to various paints (e.g. paints for building exteriors, paints for building materials, paints for metals, paints for plastics, heavy anticorrosive paints, waterproof paints for roofs). This resin composition comprises a (meth)acrylate ester-based polymer and an aqueous medium, wherein the (meth)acrylate ester-based polymer is obtained by a process including the step of polymerizing a monomer component including a polymerizable unsaturated monomer as an essential component wherein the polymerizable unsaturated monomer is a cyclohexylalkyl ester of (meth)acrylic acid wherein the cyclohexyl group may have a substituent, and wherein the (meth)acrylate ester-based polymer is dispersed in the aqueous medium.

8 Claims, No Drawings

CYCLOHEXYLALKYL (METH) ACRYLATE ESTER-BASED RESIN COMPOSITION

BACKGROUND OF THE INVENTION

A. Technical Field

The present invention relates to a novel (meth)acrylate ester-based resin composition, a novel (meth)acrylate ester-based polymer, and a novel cyclohexylalkyl ester of (meth)acrylic acid, wherein the (meth)acrylate ester-based polymer is favorable also as a constituent of the above resin composition, and wherein the cyclohexylalkyl ester of (meth)acrylic acid is used to obtain the above polymer.

In more detail, the present invention relates to a novel (meth)acrylate ester-based resin composition, a novel (meth) acrylate ester-based polymer, and a novel cyclohexylalkyl ester of (meth)acrylic acid, wherein the (meth)acrylate ester-based resin composition is, for example, favorable for various uses such as coating agents (e.g. for films, plastics, glass, paper, fibers, leather), pressure sensitive adhesives, and adhesives in addition to paints (e.g. paints for building exteriors, paints for building materials, paints for metals, paints for plastics, heavy anticorrosive paints, waterproof paints for roofs), and wherein the (meth)acrylate ester-based polymer is favorable also as a constituent of the above resin composition, and wherein the cyclohexylalkyl ester of (meth)acrylic acid is used to obtain the above polymer.

B. Background Art (Meth)acrylic resin paints are superior to alkyd resin paints or other various resin paints in respect to weather resistance, chemical resistance, and water resistance, and further have the advantage of being easily usable, because the (meth)acrylic resin paints do not need to, like conventional curing type resins, be mixed with curing agents such as polyisocyanate compounds and aminoplast resins. Therefore, the (meth)acrylic resin paints are used in wide fields of such as building materials, woodworking, roofing tiles, paper, and metals, and desired to be still more excellent in respect to the above properties.

Coating films of paints which are used in such as building fields have so far had problems of undergoing such as hazing, discoloring, blistering, and cracking when being exposed to wind, rain, or sunlight for a long time. Therefore, in the case where high durability and high weather resistance for a long time are needed, such as solvent type fluororesin paints, acrylic silicone-based resin paints, or resin paints as obtained by introducing low hygroscopic functional groups, ultraviolet stable groups, or ultraviolet absorbent groups into polymers have been used.

On the other hand, as to the (meth)acrylic resin paints, cyclohexyl (meth)acrylate is particularly favorable and well known as a polymerizable unsaturated monomer having the low hygroscopic functional group effective for achieving the high weather resistance. However, in the case where the cyclohexyl (meth)acrylate content of polymers is too high, the resultant coating films are inferior in flexibility, processability, or adhesion. Therefore, the range of the use of the cyclohexyl (meth)acrylate is limited. In addition, the cyclohexyl (meth)acrylate has problems in that the cyclohexyl group, which has great effects on the enhancement of such as weather resistance and heat resistance, is easily eliminated therefrom by such as hydrolysis.

Furthermore, in recent years, such as environmental pollution and influence on human bodies are becoming considered, therefore it is desired to increase the use of water base paints, such as emulsion paints, in place of solvent type paints.

SUMMARY OF THE INVENTION

A. Object of the Invention

An object of the present invention is to provide a novel (meth)acrylate ester-based resin composition, a novel (meth) acrylate ester-based polymer, and a novel cyclohexylalkyl ester of (meth)acrylic acid, wherein the (meth)acrylate ester-based resin composition, for example, exhibits various good properties such as weather resistance, heat resistance, water resistance, acid resistance, alkali resistance, warm water resistance, impact resistance, flexibility, processability, adhesion, hardness, elongation, transparency, luster, fleshy property, mirroring property, pigment dispersibility, and driability when being used for various uses such as coating agents (e.g. for films, plastics, glass, paper, fibers, leather), pressure sensitive adhesives, and adhesives in addition to various paints (e.g. paints for building exteriors, paints for building materials, paints for metals, paints for plastics, heavy anticorrosive paints, waterproof paints for roofs), and wherein the (meth)acrylate ester-based polymer is favorable also as a constituent of the above resin composition and excellent in such as weather resistance, heat resistance, impact resistance, flexibility, processability, and elongation, and wherein the cyclohexylalkyl ester of (meth)acrylic acid is used to obtain the above polymer.

B. Disclosure of the Invention

The present inventors diligently studied to solve the above problems. As a result, they have completed the present invention by finding out that the above problems could be solved all at once by a resin composition comprising a (meth)acrylate ester-based polymer which is in a dispersed state and is obtained by a process including the step of polymerizing a monomer component including a (meth) acrylate ester as an essential component wherein the (meth) acrylate ester possesses a specific cyclohexylalkyl group as an introduced ester group.

In addition, the present inventors have completed the present invention by thinking out a cyclohexylalkyl ester of (meth)acrylic acid as a polymerizable unsaturated monomer and finding out that the above problems could be solved all at once by a (meth)acrylate ester-based polymer which is obtained by a process including the step of polymerizing a monomer component including this cyclohexylalkyl ester of (meth)acrylic acid as an essential component, wherein the ester group in the cyclohexylalkyl ester of (meth)acrylic acid is a cyclohexylalkyl group in which the cyclohexyl ring is a 3- and/or 4-substituted one and is bonded through a (poly) methylene group (alkylene group).

That is to say, a (meth)acrylate ester-based resin composition, according to the present invention, comprises a (meth)acrylate ester-based polymer and an aqueous medium, wherein the (meth)acrylate ester-based polymer is obtained by a process including the step of polymerizing a monomer component including a polymerizable unsaturated monomer as an essential component wherein the polymerizable unsaturated monomer is a cyclohexylalkyl ester of (meth)acrylic acid wherein the cyclohexyl group may have a substituent, and wherein the (meth)acrylate ester-based polymer is dispersed in the aqueous medium.

In addition, a (meth)acrylate ester-based polymer, according to the present invention, is obtained by a process including the step of polymerizing a monomer component including a polymerizable unsaturated monomer as an essential component wherein the polymerizable unsaturated monomer is a cyclohexylalkyl ester of (meth)acrylic acid wherein the cyclohexylalkyl ester of (meth)acrylic acid is denoted by the following general formula (2):

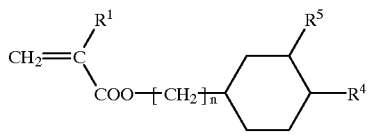

(2)

wherein:
$R^1$ is a hydrogen atom or methyl group;
each of $R^4$ and $R^5$ is a hydrogen atom or organic residue wherein the case where $R^4$ and $R^5$ are simultaneously hydrogen atoms is excluded; and
n is an integer of 1 to 4.

In addition, another (meth)acrylate ester-based polymer, according to the present invention, has a number-average molecular weight of 1,000 to 20,000,000 and a structural unit that is derived from a cyclohexylalkyl ester of (meth)acrylic acid and denoted by the following general formula (3):

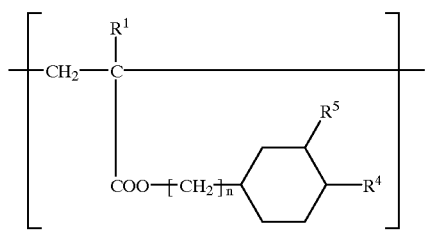

(3)

wherein: $R^1$ is a hydrogen atom or methyl group;
each of $R^4$ and $R^5$ is a hydrogen atom or organic residue wherein the case where $R^4$ and $R^5$ are simultaneously hydrogen atoms is excluded; and
n is an integer of 1 to 4.

In addition, a cyclohexylalkyl ester of (meth)acrylic acid, according to the present invention, is denoted by the following general formula (2):

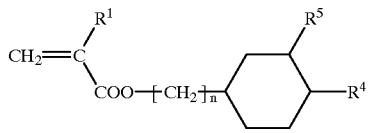

(2)

wherein: $R^1$ is a hydrogen atom or methyl group;
each of $R^4$ and $R^5$ is a hydrogen atom or organic residue wherein the case where $R^4$ and $R^5$ are simultaneously hydrogen atoms is excluded; and
n is an integer of 1 to 4.

These and other objects and the advantages of the present invention will be more fully apparent from the following detailed disclosure.

DETAILED DESCRIPTION OF THE INVENTION

<<(Meth)acrylate Ester-based Resin Composition>>
(Resin Composition):

The (meth)acrylate ester-based resin composition, according to the present invention, comprises the above (meth) acrylate ester-based polymer and an aqueous medium, wherein the aforementioned polymer is dispersed in the aforementioned aqueous medium. Incidentally, as to the above (meth)acrylate ester-based polymer, only one kind thereof may be used, or two or more kinds thereof may be used together.

As to the aforementioned aqueous medium, usually, water is favorably used, but there is no especial limitation thereto and, if necessary, hydrophilic solvents such as lower alcohols and ketones are also favorably used together with water.

The above phrase "the aforementioned polymer is dispersed in the aforementioned aqueous medium" means that the resin composition is what is called a heterogeneous resin composition in which the aforementioned polymer exists in the form of fine particles without entirely being dissolved in the aforementioned aqueous medium, and it is favorable to consider that the above phrase is used herein to the effect of excluding the case where the resin composition is what is called a homogeneous resin composition in which the aforementioned polymer is in a state entirely dissolved in the aforementioned aqueous medium. Particularly in the present invention, the resin composition is favorably either an emulsion type in which the aforementioned polymer as obtained by emulsion polymerization is dispersed as an emulsion polymer in the aqueous medium, or a dispersion type in which the aforementioned polymer as obtained by other polymerization methods is forcedly emulsified and thereby dispersed in the aqueous medium. However, there is no limitation only thereto.

The process for preparing the (meth)acrylate ester-based resin composition according to the present invention is not especially limited, but favorable examples thereof include two preparation processes which relate to the above emulsion type and dispersion type resin compositions.

As to the aforementioned emulsion type, the resin composition according to the present invention is favorably obtained by a process including the steps of synthesizing the (meth)acrylate ester-based polymer according to the present invention as an emulsion polymer by conventional emulsion polymerization and then dispersing the resultant polymer into the aqueous medium. As to the aforementioned aqueous medium, usually, water is favorably used, but there is no especial limitation thereto and, if necessary, hydrophilic solvents such as lower alcohols and ketones are also favorably used together with water.

As to the aforementioned dispersion type, the resin composition according to the present invention is favorably obtained by a process including the steps of synthesizing the (meth)acrylate ester-based polymer according to the present invention by methods other than emulsion polymerization, for example, by any method of suspension polymerization, bulk polymerization, and solution polymerization (although there is no especial limitation thereto), and then forcedly emulsifying and dispersing the resultant polymer as a finely particulate (colloidal) polymer into the aqueous medium with an emulsifier or dispersant.

In the case of an emulsion type aqueous resin composition in particular of the aforementioned emulsion type resin compositions, its diffusion is the highest of so-called aqueous resin compositions, and its general features that can favorably be enumerated are, for example, milky external appearance, relatively large molecular weights of polymer particles, and high solid content in the coating step. In addition, its particle diameter is favorably in the range of 0.01 to 50 μm, more favorably 0.02 to 20 μm, still more favorably 0.03 to 1 μm. Its typical uses are not especially limited, but favorable examples thereof include coating agents (e.g. for films, plastics, glass, paper, fibers, leather), pressure sensitive adhesives, and adhesives in addition to paints (e.g. paints for building exteriors, paints for building materials, paints for metals, paints for plastics, heavy anti-corrosive paints, waterproof paints for roofs).

In the case of a water-based dispersion type aqueous resin composition in particular of the aforementioned dispersion type resin compositions, its general features that can favorably be enumerated are, for example, translucent or milky external appearance, medium molecular weights of polymer particles as compared with the emulsion type, and relatively high solid content in the coating step, and its particle diameter is favorably in the range of 0.01 to 0.5 µm, more favorably 0.02 to 0.2 µm. In addition, its properties that can favorably be enumerated are excellent aspects in such as driability, luster, hardness, water resistance, and mechanical stability. However, neither the aforementioned features nor properties are especially limited to the above. Furthermore, as to coating film properties, the water-based dispersion type aqueous resin composition favorably has intermediate properties between a water-soluble aqueous resin composition, which forms a high-lustrous and fine coating film, but easily involves cissing or pitting, and the aforementioned emulsion type aqueous resin composition. Its typical uses are not especially limited, but favorable examples thereof include utilization for processing of paper and films in addition to ink and high gloss lacquers.

The content of the aforementioned (meth)acrylate ester-based polymer in the (meth)acrylate ester-based resin composition according to the present invention is favorably in the range of 5 to 90 weight %, more favorably 20 to 80 weight %, still more favorably 25 to 80 weight %, particularly favorably 25 to 75 weight %, most favorably 30 to 70 weight %, of the (meth)acrylate ester-based resin composition. In the case where the content of the aforementioned (meth)acrylate ester-based polymer deviates from the above ranges, there is an unfavorable possibility that the aforementioned resin composition according to the present invention could not sufficiently exhibit its various properties.

The (meth)acrylate ester-based resin composition according to the present invention further comprises the aqueous medium, of which the content in the aforementioned (meth)acrylate ester-based resin composition is favorably in the range of 10 to 95 weight %, more favorably 20 to 80 weight %, particularly favorably 25 to 70 weight %, most favorably 20 to 60 weight %, of the (meth)acrylate ester-based resin composition. In the case where the content of the aforementioned aqueous medium deviates from the above ranges, there is an unfavorable possibility that the aforementioned resin composition could not sufficiently exhibit its various properties.

Although not especially limited, the (meth)acrylate ester-based resin composition according to the present invention may favorably further comprise such as a compound having dispersibility or emulsifiability, in addition to the aforementioned (meth)acrylate ester-based polymer and the aforementioned aqueous medium which are essential components of the resin composition. The compound having dispersibility or emulsifiability is not especially limited, but favorably usable examples thereof include polymers having dispersibility or emulsifiability, in addition to so-called dispersants and emulsifiers.

The aforementioned dispersants and emulsifiers are not especially limited, but favorable examples thereof include those which can be used for emulsion polymerization, namely, anionic surfactants, cationic surfactants, nonionic surfactants, amphoteric surfactants, high-molecular surfactants, and polymerizable surfactants having at least one polymerizable carbon-carbon unsaturated bond per molecule.

The aforementioned polymers having dispersibility or emulsifiability are not especially limited, but favorable specific examples thereof include (partially saponified or) carboxyl-group-modified poly(vinyl alcohol), methyl cellulose, hydroxyethyl cellulose, poly(vinylpyrrolidone), polycarboxylic acid-based high-molecular emulsifiers, EO/PO block polymers, poly(vinyl alcohol), poly(sodium (meth)acrylate), poly(potassium (meth)acrylate), poly (ammonium (meth)acrylate), poly(hydroxyethyl (meth) acrylate), poly(hydroxypropyl (meth)acrylate), copolymers of at least two kinds of polymerizable monomers (which are structural units of these polymers) or copolymers of them with other monomers, and phase transfer catalysts such as crown ethers. These may be used either alone respectively or in combinations with each other.

The content of the aforementioned compound, having dispersibility or emulsifiability, in the (meth)acrylate ester-based resin composition according to the present invention is favorably in the range of 0.1 to 20 weight %, more favorably 0.2 to 10 weight %, particularly favorably 0.3 to 6 weight %, of the (meth)acrylate ester-based resin composition. In the case where the content of the aforementioned compound having dispersibility or emulsifiability deviates from the above ranges, there is an unfavorable possibility that the resin composition according to the present invention could not sufficiently exhibit its various properties. Specifically, in the case where the content of the aforementioned compound having dispersibility or emulsifiability is less than 0.1 weight %, there are disadvantages of involving the deterioration of the dispersing stability of the polymer in the resin composition according to the present invention. In addition, in the case where the aforementioned content is more than 20 weight %, there are disadvantages of involving the deterioration of such as water resistance of a coating film as formed when the aforementioned resin composition is favorably used for such as paints.

If necessary, fitly, the (meth)acrylate ester-based resin composition according to the present invention can favorably further comprise various additives, such as pigments, aggregates, and fillers (wherein the additives are not limited thereto), as other components, and these may be used either alone respectively or in combinations with each other.

The aforementioned pigment is not especially limited in kind, but favorable specific examples thereof include: inorganic pigments such as white pigments (e.g. titanium oxide, antimony trioxide, zinc white, lithopone, white lead) and color pigments (e.g. carbon black, chrome yellow, molybdate orange, red iron oxide); and organic pigments such as azo compounds (e.g. benzidine, Hansa yellow) and phthalocyanines (e.g. phthalocyanine blue). These may be used either alone respectively or in combinations with each other.

In the case where the (meth)acrylate ester-based resin composition according to the present invention is, for example, used as paints, pigments of which the weather resistance is so good as not to deteriorate the weather resistance of the resulting paint film are desirably selected from among the aforementioned pigments. For example, as to the titanium oxide which is a white pigment, the use of rutile type titanium oxide is preferable to the use of anatase type titanium oxide in respect to the weather resistance of the resulting paint film. In addition, as to the rutile type titanium oxide, chlorine process titanium oxide is preferable to sulfuric acid process titanium oxide in respect to being able to prolong the period of time of retaining and exhibiting the weather resistance.

As to the aforementioned aggregate, its kind may be either a transparent aggregate or a color aggregate. Although not especially limited, favorable specific examples of the transparent aggregate include feldspar, silica sand, silica stone, crystalline lime stone sand, glass beads, and synthetic resin beads, and favorable specific examples of the color aggregate include marble powder, granite powder, serpetinite, fluorite, color silica sand powder, and color pottery powder. These may be used either alone respectively or in combinations with each other.

In the case where the (meth)acrylate ester-based resin composition according to the present invention contains the aforementioned additives such as pigments, aggregates, and fillers, the content of these additives in the resin composition is favorably less than 40 weight % for uses for such as clear paints, and further is favorably in the range of 5 to 80 weight %, more favorably 10 to 70 weight %, still more favorably 20 to 60 weight %, for uses for such as enamel paints, in order for the additives to sufficiently exhibit their effects.

If necessary, fitly, the (meth)acrylate ester-based resin composition according to the present invention may favorably further comprise various additives other than the aforementioned pigments and aggregates, such as fillers, leveling agents, dispersants, plasticizers, stabilizers, dyes, ultraviolet absorbents, ultraviolet stabilizers, and antioxidants (wherein the other additives are not limited thereto).

The (meth)acrylate ester-based resin composition according to the present invention has a pH value in the range of favorably 1.6 to 11, more favorably 4 to 10, still more favorably 6 to 9.5. The deviation of the pH value from the above ranges has the disadvantage of having a possibility of deteriorating the properties of the resin composition according to the present invention.

The (meth)acrylate ester-based resin composition according to the present invention has a viscosity of favorably not more than 100,000 mPa·s, more favorably in the range of 5 to 50,000 mPa·s, still more favorably 10 to 20,000 mPa·s. The deviation of the viscosity from the above ranges has the disadvantage of having a possibility of deteriorating the properties of the resin composition according to the present invention.

(Polymer):

The (meth)acrylate ester-based polymer, which is an essential component of the (meth)acrylate ester-based resin composition according to the present invention, is a polymer obtained by a process including the step of polymerizing a monomer component including a polymerizable unsaturated monomer as an essential component wherein the polymerizable unsaturated monomer is a cyclohexylalkyl ester of (meth)acrylic acid. Incidentally, the cyclohexyl group in the molecular structure of the aforementioned polymerizable unsaturated monomer may have a substituent.

In addition, the aforementioned cyclohexylalkyl ester of (meth)acrylic acid (wherein the cyclohexyl group may have a substituent), which is an essential monomer component of the (meth)acrylate ester-based polymer that is an essential component of the resin composition according to the present invention, is favorably denoted by the following general formula (1):

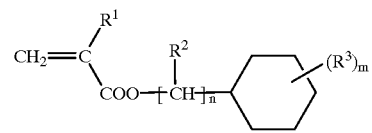

$R^1$ in the specific polymerizable unsaturated monomer as denoted by the aforementioned general formula (1) is a hydrogen atom or methyl group.

$R^2$ in the specific polymerizable unsaturated monomer as denoted by the aforementioned general formula (1) is a hydrogen atom or organic residue. In the case where the $R^2$ is an organic residue, favorable examples include 1-cyclohexylethyl (meth)acrylate (which might be referred to as cyclohexyl(methyl)methyl (meth)acrylate) although there is no especial limitation thereto. In addition, n is an integer of 1 to 4.

$R^3$ in the specific polymerizable unsaturated monomer as denoted by the aforementioned general formula (1) is an organic residue on the cyclohexyl group. In addition, m is an integer of 0 to 2. The case of m=0 denotes nonsubstitution, and the case of m=1 denotes monosubstitution, and the case of m=2 denotes disubstitution. In this case, $R^3$ may be a substituent at any position if it is on the cyclohexyl group. In addition, one kind of substituent may exist in one or more places, or at least two kinds of substituents may exist in one or more places. In the case where $R^3$ is an organic residue, examples thereof include linear, branched, or cyclic alkyl groups having 1 to 10 carbon atoms, hydroxyalkyl groups having 1 to 5 carbon atoms, alkoxyalkyl groups having 1 to 5 carbon atoms, acetoxyalkyl groups having 1 to 5 carbon atoms, and halogenated (e.g. chlorinated, brominated, or fluorinated) alkyl groups having 1 to 5 carbon atoms. Favorably used of them are alkyl groups having 1 to 4 carbon atoms, hydroxyalkyl groups having 1 to 2 carbon atoms, alkoxyalkyl groups having 1 to 2 carbon atoms, and acetoxyalkyl groups having 1 to 2 carbon atoms. As is mentioned above, the above $R^3$ may be a substituent at any position if it is on the cyclohexyl group, but favorably the position of $R^3$ is the 3- or 4-numbered position. In addition, the case where there is no substituent on the cyclohexyl group is also favorable. However, the above $R^3$ is defined as not including the epoxy-substituent structure which is seen in such as 3,4-epoxycyclohexylmethyl (meth)acrylate and 3,4-epoxycyclohexylethyl (meth)acrylate. In other words, the alicyclic epoxy ring structure is not included in the cyclohexyl group structure in the aforementioned general formula (1).

Although not especially limited, favorable specific examples of the specific polymerizable unsaturated monomer as denoted by the aforementioned general formula (1) include cyclohexylmethyl (meth)acrylate, cyclohexylethyl (meth)acrylate, cyclohexylpropyl (meth)acrylate, cyclohexylbutyl (meth)acrylate, 4-methylcyclohexylmethyl (meth)acrylate, 4-ethylcyclohexylmethyl (meth)acrylate, 4-propylcyclohexylmethyl (meth)acrylate, 4-butylcyclohexylmethyl (meth)acrylate, 4-methoxycyclohexylmethyl (meth)acrylate, 4-acetoxymethylcyclohexylmethyl (meth)acrylate, 3-methylcyclohexylmethyl (meth)acrylate, 3-ethylcyclohexylmethyl (meth)acrylate, 3-propylcyclohexylmethyl (meth)acrylate, 3-butylcyclohexylmethyl (meth)acrylate, 3-methoxycyclohexylmethyl (meth)acrylate, 3-acetoxymethylcyclohexylmethyl (meth)acrylate, 3-hydroxymethylcyclohexylmethyl (meth)acrylate, 4-methylcyclohexylethyl (meth)acrylate, 4-ethylcyclohexylethyl (meth)acrylate, 4-propylcyclohexylethyl (meth)acrylate, 4-butylcyclohexylethyl (meth)acrylate, 4-methoxycyclohexylethyl (meth)acrylate, 4-acetoxymethylcyclohexylethyl (meth)acrylate, 4-hydroxymethylcyclohexylethyl (meth)acrylate, 3-methylcyclohexylethyl (meth)acrylate, 3-ethylcyclohexylethyl (meth)acrylate, 3-propylcyclohexylethyl (meth)acrylate, 3-butylcyclohexylethyl (meth)acrylate, 3-methoxycyclohexylethyl (meth)acrylate, 3-acetoxymethylcyclohexylethyl (meth)acrylate, 3-hydroxymethylcyclohexylethyl (meth)acrylate, 4-methylcyclohexylpropyl (meth)acrylate, 4-ethylcyclohexylpropyl (meth)acrylate, 4-methoxycyclohexylpropyl (meth)acrylate, 4-acetoxymethylcyclohexylpropyl (meth)acrylate, 4-hydroxymethylcyclohexylpropyl (meth)acrylate, 3-methylcyclohexylpropyl (meth)acrylate, 3-ethylcyclohexylpropyl (meth)acrylate, 3-methoxycyclohexylpropyl (meth)acrylate, 3-acetoxymethylcyclohexylpropyl (meth)acrylate, 3-hydroxymethylcyclohexylpropyl (meth)acrylate, 4-methylcyclohexylbutyl (meth)acrylate, 4-ethylcyclohexylbutyl (meth)acrylate, 4-methoxycyclohexylbutyl (meth)acrylate, 4-acetoxymethylcyclohexylbutyl (meth)acrylate, 4-hydroxymethylcyclohexylbutyl (meth)acrylate, 3-methylcyclohexylbutyl (meth)acrylate, 3-ethylcyclohexylbutyl (meth)acrylate, 3-methoxycyclohexylbutyl (meth)acrylate, 3-acetoxymethylcyclohexylbutyl (meth)acrylate, 3-hydroxymethylcyclohexylbutyl (meth)acrylate, 2-methyl-1-cyclohexylmethyl (meth)acrylate, 2,3-dimethyl-1-cyclohexylmethyl (meth)acrylate, 2,4-dimethyl-1-cyclohexylmethyl (meth)acrylate, 2,6-dimethyl-1-cyclohexylmethyl (meth)acrylate, 2-phenyl-1-cyclohexylmethyl (meth)acrylate, 2-phenyl-3-methyl-1-cyclohexylmethyl (meth)acrylate, 2-phenyl-4-methyl-1-cyclohexylmethyl (meth)acrylate, 2-phenyl-5-methyl-1-cyclohexylmethyl (meth)acrylate, and 2-phenyl-6-methyl-1-cyclohexylmethyl (meth)acrylate. Of these, those which include isomers may be each isomer alone and/or mixtures of isomers. Favorably used of the above unsaturated monomers are 4-methylcyclohexylmethyl (meth)acrylate, 4-ethylcyclohexylmethyl (meth)acrylate, 4-methoxycyclohexylmethyl (meth)acrylate, 4-acetoxymethylcyclohexylmethyl (meth)acrylate, 3-methylcyclohexylmethyl (meth)acrylate, 3-ethylcyclohexylmethyl (meth)acrylate, 3-acetoxymethylcyclohexylmethyl (meth)acrylate, 3-hydroxymethylcyclohexylmethyl (meth)acrylate, 4-methylcyclohexylethyl (meth)acrylate, 3-methylcyclohexylethyl (meth)acrylate, 4-methylcyclohexylpropyl (meth)acrylate, 3-methylcyclohexylpropyl (meth)acrylate, 4-methylcyclohexylbutyl (meth)acrylate, and 3-methylcyclohexylbutyl (meth)acrylate.

The (meth)acrylate ester-based polymer, which is an essential component of the resin composition according to the present invention, is obtained by a process including the step of polymerizing a monomer component including the above specific polymerizable unsaturated monomer of the aforementioned general formula (1) as an essential component. The content of the aforementioned specific unsaturated monomer in the aforementioned monomer component is favorably not less than 5 weight %, more favorably not less than 10 weight %, still more favorably not less than 20 weight %, yet still more favorably not less than 25 weight %, particularly favorably not less than 30 weight %, most favorably not less than 35 weight %, in view of the properties of the resulting aforementioned (meth)acrylate ester-based polymer and further the properties of the finally obtained resin composition according to the present invention. In addition, the content of the aforementioned specific unsaturated monomer in the aforementioned monomer component is favorably not more than 95 weight %, more favorably not more than 90 weight %, still more favorably not more than 85 weight %, for enhancing the weather resistance and getting better such as property balance between impact resistance and flexibility, as concerned with processability, of the finally obtained resin composition according to the present invention.

In detail, in the step of obtaining the aforementioned (meth)acrylate ester-based polymer, it is favorable to homopolymerize the specific polymerizable unsaturated monomer of the aforementioned general formula (1) or to copolymerize this monomer with another polymerizable unsaturated monomer which is copolymerizable therewith.

Favorable examples of the process for producing the specific polymerizable unsaturated monomer of the aforementioned general formula (1) include: ① a production process comprising the step of carrying out a reaction between (meth)acrylic acid and an alcohol as denoted by the below-mentioned general formula (4); ② a production process comprising the step of carrying out a reaction between a (meth)acryloyl halide and an alcohol as denoted by the below-mentioned general formula (4); ③ a production process comprising the step of carrying out a reaction between (meth)acrylic anhydride and an alcohol as denoted by the below-mentioned general formula (4); ④ a production process comprising the step of carrying out a reaction between a (meth)acrylic acid alkyl ester and an alcohol as denoted by the below-mentioned general formula (4); and ⑤ a production process comprising the step of carrying out a reaction between (meth)acrylic acid and a carboxylate ester as denoted by the below-mentioned general formula (5). However, there is no especial limitation to these production processes. Of these production processes, particularly, production processes ①, ④, and ⑤ are favorable for such as economy.

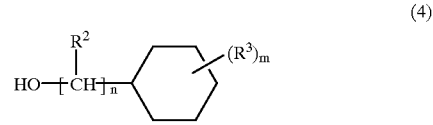

(4)

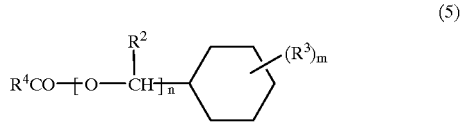

(5)

wherein: $R^2$ is a hydrogen atom or organic residue;
$R^3$ is an organic residue on the cyclohexyl group;
$R^4$ is a hydrogen atom or organic residue;
m is an integer of 0 to 2; and
n is an integer of 1 to 4.

However, the above $R^3$ is defined as not including the epoxy substituent which is seen in such as 3,4-epoxycyclohexylmethyl (meth)acrylate and 3,4-epoxycyclohexylethyl (meth)acrylate.

The aforementioned other polymerizable unsaturated monomer which is copolymerizable is not especially limited, but favorable specific examples thereof include the following:

(meth)acrylic acid alkyl esters such as methyl (meth) acrylate, ethyl (meth)acrylate, n-butyl (meth)acrylate, isobutyl (meth)acrylate, tert-butyl (meth)acrylate, sec-butyl (meth)acrylate, n-propyl (meth)acrylate, isopropyl (meth) acrylate, isoamyl (meth)acrylate, 2-ethylhexyl (meth) acrylate, isodecyl (meth)acrylate, tridecyl (meth)acrylate, cyclohexyl (meth)acrylate, n-octyl (meth)acrylate, isooctyl (meth)acrylate, n-lauryl (meth)acrylate, benzyl (meth) acrylate, dicyclopentanyl (meth)acrylate, n-stearyl (meth) acrylate, isostearyl (meth)acrylate, isobornyl (meth)acrylate, tetrahydrofurfuryl (meth)acrylate, allyl (meth)acrylate, 2-(acetoacetoxy)ethyl (meth)acrylate, and phenoxyethyl (meth)acrylate;

styrenic monomers such as styrene, α-methylstyrene, o-methylstyrene, m-methylstyrene, p-methylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-dodecylstyrene, and p-phenylstyrene;

vinyl compounds such as vinyltoluene and divinylbenzene;

vinyl esters such as vinyl acetate, vinyl propionate, vinyl chloride, vinylidene chloride, vinyl n-butyrate, vinyl benzoate, vinyl p-t-butylbenzoate, vinyl pivalate, vinyl 2-ethylhexanoate, and vinyl laurate;

(alcoholic-)hydroxyl-group-containing (meth)acrylates such as 2-hydroxyethyl (meth)acrylate, 2-hydroxypropyl (meth)acrylate, 3-hydroxypropyl (meth)acrylate, 2-hydroxybutyl (meth)acrylate, 4-hydroxybutyl (meth) acrylate, methyl(α-hydroxymethyl) acrylate, ethyl(α-hydroxymethyl) acrylate, butyl(α-hydroxymethyl) acrylate, caprolactone-modified hydroxy(meth)acrylate (trade name: Placcel F series, produced by Daicel Chemical Industries, Ltd.), 4-hydroxymethylcyclohexylmethyl (meth)acrylate, ethylene glycol mono(meth)acrylate, diethylene glycol mono(meth)acrylate, tetraethylene glycol mono(meth) acrylate, propylene glycol mono(meth)acrylate, dipropylene glycol mono(meth)acrylate, and tetrapropylene glycol mono (meth)acrylate;

carboxyl-group-containing unsaturated monomers such as acrylic acid, methacrylic acid, maleic acid, fumaric acid, crotonic acid, itaconic acid, citraconic acid, maleic anhydride, monomethyl maleate, monobutyl maleate, monomethyl itaconate, monobutyl itaconate, vinylbenzoic acid, monohydroxyethyl oxalate (meth)acrylate, dimethyl maleate, diethyl maleate, dibutyl maleate, dimethyl fumarate, diethyl fumarate, dibutyl fumarate, carboxyl-group-terminated caprolactone-modified acrylate (trade name: Placcel FA series, produced by Daicel Chemical Industries, Ltd.), and carboxyl-group-terminated caprolactone-modified methacrylate (trade name: Placcel FMA series, produced by Daicel Chemical Industries, Ltd.);

metal salts and amine salts of the carboxyl-group-containing unsaturated monomers, such as sodium acrylate and sodium methacrylate;

sulfonic-acid-group-containing unsaturated monomers such as vinylsulfonic acid, styrenesulfonic acid, and sulfoethyl (meth)acrylate;

acidic-functional-group-containing polymerizable unsaturated monomers, for example, acidic phosphate ester-based unsaturated monomers such as 2-(meth)acryloyloxyethyl acid phosphate, 2-(meth)acryloyloxypropyl acid phosphate, 2-(meth)acryloyloxy-3-chloro-propyl acid phosphate, and 2-(meth)acryloyloxyethyl phenyl phosphate;

epoxy-group-containing polymerizable unsaturated monomers such as glycidyl (meth)acrylate, α-methylglycidyl acrylate, glycidyl allyl ether, oxocyclohexylmethyl (meth)acrylate, 3,4-epoxycyclohexylmethyl acrylate (trade name: CYCLOMER A200, produced by Daicel Chemical Industries, Ltd.), α-methylglycidyl methacrylate (trade name: M-GMA, produced by Daicel Chemical Industries, Ltd.), and 3,4-epoxycyclohexylmethyl methacrylate (trade name: CYCLOMER M100, produced by Daicel Chemical Industries, Ltd.);

isocyanate-group-containing polymerizable unsaturated monomers such as 2-methacryloyloxyethyl isocyanate (trade name: Karenz MOI, produced by SHOWA DENKO Corporation), methacryloyl isocyanate (trade name: MAI, produced by Nippon Paint Co., Ltd.), and m-isopropenyl-α,α-dimethylbenzyl isocyanate (trade name: m-TMI, produced by Takeda Chemical Industries, Ltd.);

active-carbonyl-group-containing polymerizable unsaturated monomers such as acrolein, diacetone(meth) acrylamide, acetoacetoxyethyl (meth)acrylate, formylstyrol, vinyl alkyl ketones having 4 to 7 carbon atoms (e.g. vinyl methyl ketone, vinyl ethyl ketone, vinyl butyl ketone), (meth)acryloxyalkylpropenal, diacetone (meth)acrylate, and acetonyl (meth)acrylate;

silicon-containing polymerizable unsaturated monomers such as vinyltrichlorosilane, vinyltris(β-methoxyethoxy) silane, vinyltriethoxysilane, vinyltrimethoxysilane, γ-methacryloxypropyltrimethoxysilane, and trimethylsiloxyethyl methacrylate;

oxazoline-group-containing polymerizable unsaturated monomers such as 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl 2-oxazoline, 2-isopropenyl-5-methyl-2-oxazoline, and 2-isopropenyl-5-ethyl-2-oxazoline;

(poly)alkylene glycol (meth)acrylates such as methoxydiethylene glycol (meth)acrylate, methoxytetraethylene glycol (meth)acrylate, methoxydipropylene glycol (meth) acrylate, and methoxytetrapropylene glycol (meth)acrylate;

fluorine-containing polymerizable unsaturated monomers such as trifluoroethyl (meth)acrylate, tetrafluoropropyl (meth)acrylate, octafluoropentyl (meth)acrylate, heptadodecafluorodecyl acrylate, β-(perfluorooctyl)ethyl (meth) acrylate, hexafluoropropyl methacrylate, and perfluorooctylethyl (meth)acrylate;

nitrogen-atom-containing polymerizable unsaturated monomers such as (meth)acrylamide, N,N-dimethylaminopropylacrylamide, N-isopropylacrylamide, t-butylacrylamide, methylenebis(meth)acrylamide, N-methoxymethylacrylamide, N-ethoxymethylacrylamide, N-butoxymethylacrylamide, N-methylol(meth)acrylamide, N,N'-dimethylaminoethyl (meth)acrylate, N,N'-diethylaminoethyl (meth)acrylate, N-methyl-N-vinylformamide, dimethylaminoethyl methacrylate sulfate salts, N-vinylpyridine, N-vinylimidazole, N-vinylpyrrol, N-vinylpyrrolidone, diacetoneacrylamide, N-phenylmaleimide, N-cyclohexylmaleimide, and (meth) acrylonitrile;

multifunctional polymerizable unsaturated monomers such as (poly)ethylene glycol di(meth)acrylate, (poly) propylene glycol di(meth)acrylate, (poly)butylene glycol di(meth)acrylate, EO-modified trimethylolpropane triacrylate, trimethylolpropane triacrylate, pentaerythritol tetraacrylate, and dipentaerythritol hexaacrylate;

vinyl ethers such as vinyl methyl ether, vinyl ethyl ether, vinyl isopropyl ether, vinyl n-propyl ether, vinyl isobutyl ether, vinyl n-butyl ether, vinyl n-amyl ether, vinyl isoamyl ether, vinyl 2-ethylhexyl ether, vinyl n-octadecyl ether, cyanomethyl vinyl ether, 2,2-dimethylaminoethyl vinyl ether, 2-chloroethyl vinyl ether, β-difluoromethyl vinyl ether, benzyl vinyl ether, phenyl vinyl ether, and divinyl ether;

allyl esters such as allyl acetate and allyl benzoate;

allyl ethers such as allyl ethyl ether, allyl glycidyl ether, and allyl phenyl ether;

ultraviolet-absorbent polymerizable unsaturated monomers such as 2-[2'-hydroxy-5'-(meth)acryloyloxyethylphenyl]-2H-benzotriazole, 2-[2'-hydroxy-5'-(meth)acryloyloxypropylphenyl]-2H-benzotriazole, 2-[2'-hydroxy-5'-(meth)acryloyloxyhexylphenyl]-2H-benzotriazole, 2-[2'-hydroxy-3'-tert-butyl-5'-(meth)acryloyloxyethylphenyl]-2H-benzotriazole, 2-[2'-hydroxy-3'-tert-butyl-5'-(meth)acryloyloxyethylphenyl]-5-chloro-2H-benzotriazole, 2-[2'-hydroxy-5'-tert-butyl-3'-(meth)acryloyloxyethylphenyl]-2H-benzotriazole, 2-[2'-hydroxy-5'-(meth)acryloyloxyethylphenyl]-5-chloro-2H-benzotriazole, 2-[2'-hydroxy-5'-(meth)acryloyloxyethylphenyl]-5-methoxy-2H-benzotriazole, 2-[2'-hydroxy-5'-(meth)acryloyloxyethylphenyl]-5-cycno-2H-benzotriazole, 2-[2'-hydroxy-5'-(meth)acryloyloxyethylphenyl]-5-t-butyl-2H-benzotriazole, 2-[2'-hydroxy-5'-(β-methacryloyloxyethoxy)-3'-tert-butylphenyl]-4-tert-butyl-2H-benzotriazole, 2-hydroxy-4-methacryloxybenzophenone, 2-hydroxy-4-(2-hydroxy-3-methacryloyloxy)propoxybenzophenone, 2-hydroxy-4-(2-methacryloxy)ethoxybenzophenone, and 2-hydroxy-4-vinyloxycarbonylmethoxybenzophenone; and ultraviolet-stable polymerizable unsaturated monomers such as 4-(meth)acryloyloxy-2,2,6,6-tetramethylpiperidine, 4-(meth)acryloyloxy-1,2,2,6,6-pentamethylpiperidine, 4-(meth)acryloylamino-2,2,6,6-tetramethylpiperidine, 4-(meth)acryloylamino-1,2,2,6,6-pentamethylpiperidine, 4-cyano-4-(meth)acryloylamino-2,2,6,6-tetramethylpiperidine, 4-crotonoyloxy-2,2,6,6-tetramethylpiperidine, 4-crotonoylamino-2,2,6,6-tetramethylpiperidine, 1-(meth)acryloyl-4-(meth)acryloylamino-2,2,6,6-tetramethylpiperidine, 1-(meth)acryloyl-4-cyano-4-(meth)acryloylamino-2,2,6,6-tetramethylpiper idine, and 1-crotonoyl-4-crotonoyloxy-2,2,6,6-tetramethylpiperidine.

These other polymerizable unsaturated monomers may be used either alone respectively or in combinations with each other.

Selected from among the above other polymerizable unsaturated monomers favorably for sufficient exhibition of the effects of the present invention are (meth)acrylic acid alkyl esters, (alcoholic-)hydroxyl-group-containing (meth)acrylates, acidic-functional-group-containing (meth)acrylates (e.g. carboxyl-group-containing unsaturated monomers, metal salts and amine salts of the carboxyl-group-containing unsaturated monomers, sulfonic-acid-group-containing unsaturated monomers, acidic-functional-group-containing polymerizable unsaturated monomers (such as acidic phosphate ester-based unsaturated monomers)), vinyl compounds, fluorine-containing polymerizable unsaturated monomers, silicon-containing polymerizable unsaturated monomers, epoxy-group-containing polymerizable unsaturated monomers, ultraviolet-stable polymerizable unsaturated monomers, and ultraviolet-absorbent polymerizable unsaturated monomers. Particularly favorable are (meth)acrylic acid alkyl esters, (alcoholic-)hydroxyl-group-containing (meth)acrylates, acidic-functional-group-containing (meth)acrylates, and vinyl compounds. However, these other polymerizable unsaturated monomers are not especially limited, and they may be used either alone respectively or in combinations with each other.

The content of the aforementioned other polymerizable unsaturated monomers in the aforementioned monomer components is not especially limited, but is favorably outside the range of the content of the aforementioned specific polymerizable unsaturated monomers in the aforementioned monomer components.

The process (polymerization process) for producing the (meth)acrylate ester-based polymer, which is an essential component of the resin composition according to the present invention, is not especially limited, but examples thereof as favorably used include conventional various processes which utilize such as heat, ultraviolet rays, radiations, electron beams, and radical polymerization initiators, namely, such as emulsion polymerization, suspension polymerization, bulk polymerization, and solution polymerization.

The process for preparing the (meth)acrylate ester-based polymer, which is an essential component of the resin composition according to the present invention, is not especially limited, but can favorably be exemplified by two preparation processes, namely, an emulsion type polymerization process and a dispersion type polymerization process.

In the aforementioned emulsion type polymerization, it is favorable that the (meth)acrylate ester-based polymer according to the present invention is synthesized as an emulsion polymer by polymerizing the monomer component by conventional emulsion polymerization using the aqueous medium. This emulsion polymer disperses into the aqueous medium so easily as to favorably give the resin composition according to the present invention. As to the aforementioned aqueous medium, usually, water is favorably used, but there is no especial limitation thereto and, if necessary, hydrophilic solvents such as lower alcohols and ketones are also favorably used together with water.

In the aforementioned dispersion type polymerization, it is favorable that the (meth)acrylate ester-based polymer according to the present invention is synthesized by methods other than conventional emulsion polymerization, for example, by any method of suspension polymerization, bulk polymerization, and solution polymerization (although there is no especial limitation thereto). However, it is favorable for finally obtaining the resin composition according to the present invention that the polymer is forcedly emulsified and dispersed as a finely particulate (colloidal) polymer into the aqueous medium with an emulsifier or dispersant after being synthesized.

Incidentally, in the aforementioned dispersion type polymerization, for example, it is favorable for synthesizing the (meth)acrylate ester-based polymer (which is an essential component of the resin composition according to the present invention) by suspension polymerization that the aforementioned monomer component is polymerized by adding a polymerization initiator soluble in the aforementioned monomer component while vigorously stirring the monomer component in the aforementioned aqueous medium. In the suspension polymerization, usually, a dispersant is added in the case where the dispersed oil droplets of the aforementioned monomer component need to be stabilized. The synthesized aforementioned polymer favorably takes the form of the finely particulate (colloidal) polymer as forcedly emulsified and dispersed in the aqueous medium with the emulsifier or dispersant.

In addition, hereinafter, a detailed description is given about the case where the (meth)acrylate ester-based polymer, which is an essential component of the resin composition according to the present invention, is obtained by the aforementioned emulsion polymerization.

In the aforementioned emulsion polymerization, basically, it is favorable that the monomer component to be polymerized is emulsified into the aqueous medium such as water with an emulsifier (surfactant) and then polymerized with a polymerization initiator soluble in the aforementioned aqueous medium. Thereby an emulsion type resin as polymer particles, in other words, an emulsion polymer, can favorably be obtained.

Various improvements are made upon the structure of this emulsion polymer or the process for preparing it, and the technical mode of the aforementioned emulsion polymerization is not especially limited, but can be classified as follows. That is to say, it can favorably be exemplified by: a particle diameter control technique for super-fining or coarsening of particles; an emulsifier deletion technique for preparation of a soap-free emulsion; a profiled particle emulsion preparation technique for profiling of particle surfaces or hollowing of particles; a technique for preparation of a heterophase-structured emulsion such as polymer/polymer or wax/polymer; a technique for preparation of a crosslinking type emulsion such as normal temperature crosslinking type or baking type; and other techniques such as living emulsion polymerization, water-soluble polymer preparation, grafting, and solvent-swelling type emulsion preparation.

In the case where the aforementioned polymer is obtained by using the aforementioned emulsion polymerization or where the aforementioned polymer particles which disperse into the aforementioned aqueous medium are obtained after using the polymerization processes other than the aforementioned emulsion polymerization, examples of usable emulsifiers include anionic surfactants, cationic surfactants, nonionic surfactants, amphoteric surfactants, high-molecular surfactants, and polymerizable surfactants having at least one polymerizable carbon-carbon unsaturated bond per molecule. These may be used either alone respectively or in combinations with each other.

The aforementioned anionic surfactant is not especially limited, but favorable specific examples thereof include: alkaline-metal alkyl sulfates such as sodium dodecyl sulfate and potassium dodecyl sulfate; ammonium alkyl sulfates such as ammonium dodecyl sulfate; sodium dodecyl polyglycol ether sulfate, sodium sulfocinnoate, and alkaline-metal salts of sulfonated paraffin; alkylsulfonates such as ammonium salts of sulfonated paraffin; fatty acid salts such as sodium laurate; alkylarylsulfonates such as sodium dodecylbenzenesulfonate and alkaline-metal sulfates of alkali phenol hydroxyethylene; higher-alkylnaphthalenesulfonate salts, naphthalenesulfonic acid-formalin condensation products, dialkylsulfosuccinate salts, polyoxyethylene alkyl sulfate salts, and polyoxyethylene alkylaryl sulfate salts.

The aforementioned cationic surfactant is not especially limited, but favorable specific examples thereof include triethanolamine oleate and triethanolamine abietate.

The aforementioned nonionic surfactant is not especially limited, but favorable specific examples thereof include: polyoxyethylene alkyl ethers, polyoxyethylene alkyl aryl ethers, sorbitan fatty acid esters, polyoxyethylene sorbitan fatty acid esters, and fatty acid monoglycerides such as glycerol monolaurate; poly(oxyethylene-oxypropylene) copolymers, and products formed by condensation of ethylene oxide with fatty acid amines, amides, or acids.

The aforementioned high-molecular surfactant is not especially limited, but favorable specific examples thereof include: poly(vinyl alcohol), poly(sodium (meth)acrylate), poly(potassium (meth)acrylate), poly(ammonium (meth)acrylate), poly(hydroxyethyl (meth)acrylate), poly(hydroxypropyl (meth)acrylate), copolymers of at least two kinds of polymerizable monomers (which are structural units of these polymers) or copolymers of them with other monomers, and phase transfer catalysts such as crown ethers.

The aforementioned polymerizable surfactant is not especially limited, but favorable specific examples thereof include: anionic polymerizable surfactants such as sodium propenyl-2-ethylhexylbenzenesulfosuccinate, sulfate esters of polyoxyethylene (meth)acrylate, ammonium polyoxyethylene alkylpropenyl ether sulfates, and phosphate esters of polyoxyethylene (meth)acrylate; and nonionic polymerizable surfactants such as polyoxyethylene alkylbenzene ether (meth)acrylate and polyoxyethylene alkyl ether (meth)acrylate.

The amount of the aforementioned emulsifier, as used, is not especially limited, but is specifically in the range of favorably 0.1 to 20 weight %, more favorably 0.2 to 10 weight %, still more favorably 0.3 to 6 weight %, relative to the total weight of the monomer component including the polymerizable unsaturated monomer of the general formula (1) as an essential component. In the case where the amount of the aforementioned emulsifier as used is smaller than 0.1 weight % relative to the total weight of the monomer component, there are disadvantages of involving the deterioration of the dispersing stability of the polymer in the resin composition according to the present invention. In the case where the amount of the aforementioned emulsifier is larger than 20 weight %, there are disadvantages of involving the deterioration of such as water resistance of a coating film as formed when the aforementioned resin composition is favorably used for such as paints.

The content of the aforementioned aqueous medium in the resin composition according to the present invention is such that the content of the monomer component including the polymerizable unsaturated monomer of the general formula (1) as an essential component is favorably in the range of 10 to 95 weight %, more favorably 20 to 80 weight %, particularly favorably 25 to 70 weight %, most favorably 20 to 60 weight %, of the resin composition according to the present invention.

The above radical polymerization initiator, as used for such as the aforementioned emulsion polymerization, is not especially limited, but favorable specific examples thereof include: azo initiators such as 2,2'-azobisisobutyronitrile, 2,2'-azobis(2-amidinopropane) dihydrochloride, 4,4'-azobis(4-cyanopentanoic acid), 2,2'-azobis(2-methylbutyronitrile), and 2,2'-azobis(2,4-dimethylvaleronitrile); and peroxide initiators such as persulfate salts (e.g. potassium persulfate), hydrogen peroxide, peracetic acid, benzoyl peroxide, di-t-butyl peroxide, 1,1-bis(t-butylperoxy)-3,3,5-trimethylcyclohexane, t-butylperoxy-2-ethylhexanoate, and t-butyl hydroperoxide. In addition, on this occasion, it is also favorable to form redox initiators by combining the above peroxide initiators with reducing agents such as sodium hydrogensulfite, L-ascorbic acid, Rongalit, and sodium metabisulfite.

In addition, although not especially limited, various transition metal ions, specifically, such as ferric sulfate, cupric sulfate, ferric chloride, and cupric chloride, are favorably usable as polymerization promotors.

The aforementioned radical polymerization initiator is used in a ratio of favorably 0.01 to 20 weight %, more favorably 0.05 to 10 weight %, still more favorably 0.1 to 10 weight %, to the total weight of the monomer component including the polymerizable unsaturated monomer of the general formula (1) as an essential component. In the case of such a range of the use, excellent results are provided with regard to the yield of the resulting (meth)acrylate ester-based polymer and the economy.

The reaction temperature in the step of polymerizing the aforementioned monomer component is favorably in the range of 10 to 100° C., more favorably 40 to 90° C.

In the step of polymerizing the aforementioned monomer component, such as a chain transfer agent or adjusting agent is favorably usable for the purpose of adjusting the molecular weight, if necessary. Although not especially limited, specific examples of the favorably usable chain transfer agent or adjusting agent include: alcohols such as methanol, ethanol, propanol, and butanol; ketones such as acetone, methyl ethyl ketone, cyclohexanone, and acetophenone; aldehydes such as acetoaldehyde, n-butraldehyde, furfural, and benzaldehyde; mercaptans such as dodecylmercaptan, laurylmercaptan, thioglycolic acid, octyl thioglycolate, thioglycerol, and 2-mercaptoethanol.

The aforementioned chain transfer agent or adjusting agent is used in a ratio of favorably 0.01 to 10 weight %, more favorably 0.02 to 5 weight %, to the total weight of the monomer component including the polymerizable unsaturated monomer of the general formula (1) as an essential component.

The (meth)acrylate ester-based polymer, which is an essential component of the resin composition according to the present invention, has a number-average molecular weight in the range of favorably 1,000 to 30,000,000, more favorably 5,000 to 20,000,000, still more favorably 10,000 to 20,000,000. In the case where the aforementioned number-average molecular weight deviates from the above ranges, there is an unfavorable possibility that the properties which can be exhibited by the above (meth)acrylate ester-based polymer and further the properties of the finally obtained resin composition according to the present invention might be deteriorated.

The (meth)acrylate ester-based polymer, which is an essential component of the resin composition according to the present invention, has a glass transition temperature in the range of favorably −30 to 90° C., more favorably −20 to 80° C., still more favorably −10 to 70° C. In the case where the aforementioned glass transition temperature deviates from the above ranges, there is an unfavorable possibility that the properties which can be exhibited by the above (meth)acrylate ester-based polymer and further the properties of the finally obtained resin composition according to the present invention might be deteriorated.

The (meth)acrylate ester-based polymer, which is an essential component of the resin composition according to the present invention, has a volume-average particle diameter in the range of favorably 10 nm to 50 μm, more favorably 20 nm to 30 μm, still more favorably 30 nm to 10 μm. In the case where the aforementioned volume-average particle diameter deviates from the above ranges, there is an unfavorable possibility that the properties which can be exhibited by the above (meth)acrylate ester-based polymer and further the properties of the finally obtained resin composition according to the present invention might be deteriorated.

<<(Meth)acrylate Ester-based Polymer and Cyclohexylalkyl Ester of (Meth)acrylic Acid>>

If the cyclohexylalkyl ester of (meth)acrylic acid, according to the present invention, is a compound denoted by the below-mentioned general formula (2), it is not especially limited. In the general formula (2), the substituent denoted by $R^1$ is a hydrogen atom or methyl group, and each of the substituents denoted by $R^4$ and $R^5$ is a hydrogen atom or organic residue (wherein the case where $R^4$ and $R^5$ are simultaneously hydrogen atoms is excluded), and n is an integer of 1 to 4.

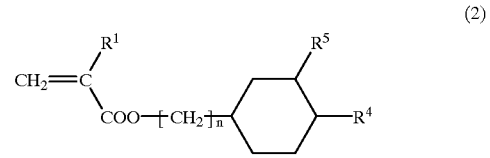

(2)

Examples of the organic residues denoted by $R^4$ and $R^5$ in the aforementioned general formula (2) include linear, branched, or cyclic alkyl groups having 1 to 10 carbon atoms, hydroxyalkyl groups having 1 to 5 carbon atoms, alkoxyalkyl groups having 1 to 5 carbon atoms, acetoxyalkyl groups having 1 to 5 carbon atoms, and halogenated (e.g. chlorinated, brominated, or fluorinated) alkyl groups having 1 to 5 carbon atoms. Favorably used of them are alkyl groups having 1 to 4 carbon atoms, hydroxyalkyl groups having 1 to 2 carbon atoms, alkoxyalkyl groups having 1 to 2 carbon atoms, and acetoxyalkyl groups having 1 to 2 carbon atoms.

Typical examples of the cyclohexylalkyl ester of (meth)acrylic acid, as denoted by the aforementioned general formula (2), is not especially limited, but, specifically, those in which the cyclohexyl ring is a 3- and/or 4-substituted one and is ester-bonded to acrylic acid through a (poly) methylene group (alkylene group) can favorably be cited from among the aforementioned specific examples of the specific polymerizable unsaturated monomer as denoted by the aforementioned general formula (1). Particularly favorable are 4-methylcyclohexylmethyl (meth)acrylate, 4-ethylcyclohexylmethyl (meth)acrylate, 4-methoxycyclohexylmethyl (meth)acrylate, 4-acetoxymethylcyclohexylmethyl (meth)acrylate, 3-methylcyclohexylmethyl (meth)acrylate, 3-ethylcyclohexylmethyl (meth)acrylate, 3-acetoxymethylcyclohexylmethyl (meth)acrylate, 3-hydroxymethylcyclohexylmethyl (meth)acrylate, 4-methylcyclohexylethyl (meth)acrylate, 3-methylcyclohexylethyl (meth)acrylate, 4-methylcyclohexylpropyl (meth)acrylate, 3-methylcyclohexylpropyl (meth)acrylate, 4-methylcyclohexylbutyl (meth)acrylate, and 3-methylcyclohexylbutyl (meth)acrylate.

The process for producing the cyclohexylalkyl ester of (meth)acrylic acid, as denoted by the aforementioned general formula (2), is not especially limited, but favorable specific examples thereof include the same as the aforementioned process for producing the specific polymerizable unsaturated monomer as denoted by the aforementioned general formula (1) except that the aforementioned general formula (4) is replaced with the below-mentioned general formula (6) and that the aforementioned general formula (5) is replaced with the below-mentioned general formula (7):

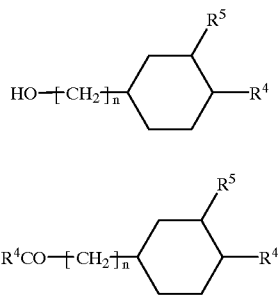

(6)

(7)

wherein:
$R^1$ is a hydrogen atom or methyl group;
each of $R^4$ and $R^5$ is a hydrogen atom or organic residue wherein the case where $R^4$ and $R^5$ are simultaneously hydrogen atoms is excluded; and
n is an integer of 1 to 4.

The (meth)acrylate ester-based polymer, according to the present invention, is a polymer obtained by a process including the step of polymerizing a monomer component including the cyclohexylalkyl ester of (meth)acrylic acid of the aforementioned general formula (2) as an essential component.

The process for producing the (meth)acrylate ester-based polymer according to the present invention is not especially limited, but this polymer is easily obtained by a process including the step of polymerizing a monomer component including the cyclohexylalkyl ester of (meth)acrylic acid of the aforementioned general formula (2) as an essential component. In addition, the (meth)acrylate ester-based polymer according to the present invention is easily produced by a process including the step of homopolymerizing the cyclohexylalkyl ester of (meth)acrylic acid of the aforementioned general formula (2) or copolymerizing this cyclohexylalkyl ester of (meth)acrylic acid with a polymerizable compound which is copolymerizable therewith.

The above polymerizable compound which is copolymerizable is not especially limited, but favorable specific examples thereof include the same as those of the "other polymerizable unsaturated monomer" which are enumerated in the aforementioned explanation of the (meth)acrylate ester-based resin composition according to the present invention. They may be used either alone respectively or in combinations with each other.

In addition, the amount of the polymerizable compound as used, namely, the ratio thereof to the cyclohexylalkyl ester of (meth)acrylic acid of the general formula (2), is not especially limited, but it is favorable for the properties of the resulting polymer that the aforementioned cyclohexylalkyl ester of (meth)acrylic acid is contained in a ratio of 1 to 100 weight %, more favorably 3 to 100 weight %, still more favorably 10 to 100 weight %, in the monomer component as used.

The process for producing the (meth)acrylate ester-based polymer is not especially limited, but usable examples thereof include conventional various processes which utilize such as heat, ultraviolet rays, radiations, electron beams, and radical polymerization initiators, namely, such as solution polymerization, emulsion polymerization, suspension polymerization, and bulk polymerization.

In the case where the polymer is obtained by using the solution polymerization process from among the above polymerization processes, usable solvents are not especially limited, but specific examples thereof include organic solvents and water wherein examples of the organic solvents include: aromatic solvents such as toluene, xylene, industrial gasoline, and reformate; ester solvents such as ethyl acetate, butyl acetate, and propylene glycol methyl ether acetate; ketone solvents such as methyl ethyl ketone, methyl isobutyl ketone, and methyl amyl ketone; aliphatic alcohol solvents such as isopropyl alcohol and n-butanol; alkylene glycol monoalkyl ether solvents such as ethylene glycol monomethyl ether, diethylene glycol monomethyl ether, and propylene glycol monomethyl ether.

The above organic solvents or water may be used in such an amount that the weight percentage of the polymerizable monomer including the cyclohexylalkyl ester of (meth)acrylic acid of the general formula (2) can be in the range of 10 to 90 weight %, favorably 20 to 80 weight %.

The above radical polymerization initiator is not especially limited, but favorable specific examples thereof include the same as those of the "radical polymerization initiator" which are enumerated in the aforementioned explanation of the (meth)acrylate ester-based resin composition according to the present invention.

The above radical polymerization initiator may be used in such an amount that the ratio thereof to the total weight of the polymerizable monomer including the cyclohexylalkyl ester of (meth)acrylic acid of the general formula (2) can be in the range of 0.05 to 20 weight %, favorably 0.1 to 10 weight %. The amount of the radical polymerization initiator as used in such a range is favorable in respect to the yield and the economy.

The reaction temperature in the step of carrying out the copolymerization is favorably in the range of room temperature to 200° C., more favorably 40 to 150° C.

Furthermore, a chain transfer agent or adjusting agent may be used for the purpose of adjusting the molecular weight, if necessary. The above chain transfer agent or adjusting agent is not especially limited, but favorable specific examples thereof include the same as those of the "chain transfer agent or adjusting agent" which are enumerated in the aforementioned explanation of the (meth)acrylate ester-based resin composition according to the present invention.

The above chain transfer agent or adjusting agent may be used in such an amount that the ratio thereof to the total weight of the polymerizable monomer including the cyclohexylalkyl ester of (meth)acrylic acid of the general formula (2) can be in the range of 0.01 to 10 weight %, favorably 0.02 to 5 weight %.

The emulsifier (surfactant) which is usable in the case where the polymer is obtained by using the emulsion polymerization from among the aforementioned polymerization processes is not especially limited, but favorable specific examples thereof include the same as those of the "anionic surfactants, cationic surfactants, nonionic surfactants, amphoteric surfactants, high-molecular surfactants, and polymerizable surfactants having at least one polymerizable carbon-carbon unsaturated bond per molecule" which are enumerated in the aforementioned explanation of the (meth)acrylate ester-based resin composition according to the present invention. These may be used either alone respectively or in combinations with each other.

The amount of the above emulsifier, as used, is not especially limited, but is specifically in the range of favorably 0.1 to 50 weight %, more favorably 1 to 10 weight %, relative to the total weight of the polymerizable monomer including the cyclohexylalkyl ester of (meth)acrylic acid of the general formula (2). In addition, examples of the radical polymerization initiator, as used for the emulsion polymerization, include: azo compounds such as 2,2'-azobisisobutyronitrile, 2,2'-azobis(2-amidinopropane) dihydrochloride, and 4,4'-azobis(4-cyanopentanoic acid); and peroxides such as persulfate salts (e.g. potassium persulfate), hydrogen peroxide, peracetic acid, benzoyl peroxide, and di-t-butyl peroxide. In addition, on this occasion, it is also possible to form redox initiators by combining the above peroxides with reducing agents such as sodium hydrogensulfite and L-ascorbic acid.

In addition, another (meth)acrylate ester-based polymer, according to the present invention, is a polymer which has a number-average molecular weight of 1,000 to 20,000,000 and a structural unit as denoted by the following general formula (3):

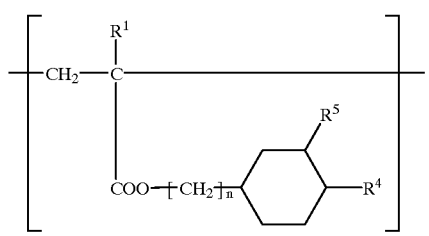

(3)

In the structural unit of the aforementioned general formula (3), the definition of each of the substituents denoted by $R^1$, $R^4$ and $R^5$ in this formula is the same as that for the (meth)acrylate ester of the aforementioned general formula (2).

Structural units other than the structural unit of the aforementioned general formula (3), which constitutes the (meth)acrylate ester-based polymer according to the present invention, are not especially limited, but the content of the structural unit of the aforementioned general formula (3) in the aforementioned (meth)acrylate ester-based polymer is favorably in the range of 1 to 100 weight %, more favorably 3 to 100 weight %, still more favorably 10 to 100 weight %, of the aforementioned polymer in view of its properties. Examples of structural units other than the structural unit of the aforementioned general formula (3) include structural units derived from the aforementioned polymerizable compounds which are copolymerizable.

The degree of polymerization of the (meth)acrylate ester-based polymer comprising the structural unit of the aforementioned general formula (3) as an essential component is favorably such a value as giving the number-average molecular weight in the range of 1,000 to 20,000,000 more favorably 2,000 to 10,000,000, most favorably 3,000 to 5,000,000.

The (meth)acrylate ester-based polymer comprising the structural unit of the aforementioned general formula (3) as an essential component is, for example, is obtained by the same production process as the aforementioned process for producing the (meth)acrylate ester-based polymer.
(Effects and Advantages of the Invention)

The present invention can provide a novel (meth)acrylate ester-based resin composition, a novel (meth)acrylate ester-based polymer, and a novel cyclohexylalkyl ester of (meth) acrylic acid, wherein the (meth)acrylate ester-based resin composition, for example, exhibits various good properties such as weather resistance, heat resistance, water resistance, acid resistance, alkali resistance, warm water resistance, impact resistance, flexibility, processability, adhesion, hardness, elongation, transparency, luster, fleshy property, mirroring property, pigment dispersibility, and driability when being used for various uses such as coating agents (e.g. for films, plastics, glass, paper, fibers, leather), pressure sensitive adhesives, and adhesives in addition to various paints (e.g. paints for building exteriors, paints for building materials, paints for metals, paints for plastics, heavy anti-corrosive paints, waterproof paints for roofs), and wherein the (meth)acrylate ester-based polymer is favorable also as a constituent of the above resin composition and excellent in such as weather resistance, heat resistance, impact resistance, flexibility, processability, and elongation, and wherein the cyclohexylalkyl ester of (meth)acrylic acid is used to obtain the above polymer.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited thereto. Incidentally, hereinafter, the "weight part(s)" and the "weight %" might be referred to simply as "part(s)" and "%" respectively.
(Measurement of Nonvolatile Content):

About 1 g of specimen was weighed out and then dried in a hot-air drying oven of 105° C. for 1 hour. The resultant drying residue was taken as the nonvolatile content, and its ratio to what the weight of the specimen had been before the drying was indicated by weight %.
(Measurement of Viscosity):

The viscosity was measured at 30 $min^{-1}$, 25° C. with a BM type viscometer (produced by Tokyo Instruments Co., Ltd.), when the rotor was selected according to the viscosity.
(Measurement of pH):

The pH value was measured at 25° C. with a pH meter (F-23, produced by Horiba Seisakusho Co., Ltd.).
(Minimum Film Formation Temperature: MFT):

The specimen was coated onto a glass plate (which was put on a thermal gradient testing machine) by using an applicator of 0.2 mm and then dried, and the temperature at which the resultant coating film cracked was taken as the minimum film formation temperature (MFT).
(Measurement of Particle Diameter):

The particle diameter was measured with a particle diameter measurement apparatus by the dynamic light scattering method (NICOMP Model 370, produced by HIAC/ROYCO INSTRUMENTS DIVISION Co., Ltd.). The particle diameter was indicated as the volume-average particle diameter.
(Calculated Tg):

The calculated Tg of a polymer comprising monomer components was calculated by the following Fox's equation:

$$1/Tg=\Sigma(Wn/Tgn)/100$$

wherein: Wn is weight % of monomer n; and Tgn is Tg (absolute temperature) of a homopolymer of the monomer n. After the calculation, Tg (absolute temperature) is treated by converting it into Tg (° C.).

EXAMPLE 1

A separable flask, as equipped with a stirrer, a thermometer, a condenser, a dropper, and a nitrogen gas-introducing tube, was charged with 82 parts of deionized water and then heated to 75° C. under a nitrogen gas flow. Next, 10 weight % of a pre-emulsion mixture was added thereto wherein the pre-emulsion mixture had been prepared by adding 50 parts of 4M-CHM-MA (4-methylcyclohexylmethyl methacrylate), 20 parts of MMA (methyl methacrylate), 29 parts of 2EHA (2-ethylhexyl acrylate), and 1 part of AA (acrylic acid) to an aqueous solution comprising 1.5 parts of Nonypol 200 (polyoxyethylene nonyl phenyl ether, produced by Sanyo Kasei Co., Ltd.), 1.5 parts of Hitenol N-08 (ammonium polyoxyethylene nonyl phenyl ether sulfonate, produced by Dai-ichi Kogyo Seiyaku Co., Ltd.), and 34 parts of deionized water. Subsequently, 10 parts of a 3% aqueous potassium persulfate solution was added into the flask, and then its internal temperature was raised to 80° C. over a period of 15 minutes. Thereafter, the remaining 90 weight % of the pre-emulsion mixture was dropwise added into the flask over a period of 3 hours, and then the flask was retained at the same temperature as the above for 1 hour. After the flask had been cooled, 0.7 part of a 25% aqueous ammonia solution was added into the flask to carry out neutralization, thus obtaining a resin composition of Example 1 (hereinafter referred to as resin composition (1)) having a nonvolatile content of 45.0%, a viscosity of 350 mPa·s (as measured with the BM type viscometer (produced by Tokyo Instruments Co., Ltd.)), a pH value of 8.3, a minimum film formation temperature (MFT) of 22° C., a volume-average particle diameter of 150 nm, and a calculated Tg of 10° C.

EXAMPLES 2 TO 8

Resin compositions of Examples 2 to 8 (hereinafter referred to as resin compositions (2) to (8)) were obtained in the same way as of Example 1 except that the polymerizable monomer components as used in Example 1 were changed to those which are shown in Table 1. The resultant resin compositions (2) to (8) were measured by the nonvolatile content, the viscosity, the pH value, the MFT the volume-average particle diameter, and the calculated Tg in the same way as of Example 1. The results thereof are shown in Table 3.

Comparative Examples 1 to 3

Resin compositions of Comparative Examples 1 to 3 (hereinafter referred to as comparative resin compositions (1) to (3)) were obtained in the same way as of Example 1 except that the polymerizable monomer components as used in Example 1 were changed to those which are shown in Table 2. The resultant comparative resin compositions (1) to (3) were measured by the nonvolatile content, the viscosity, the pH value, the MFT the volume-average particle diameter, and the calculated Tg in the same way as of Example 1. The results thereof are shown in Table 4.

Incidentally, the abbreviations in Tables are as follows:

CHM-MA: cyclohexylmethyl methacrylate
CHE-MA: cyclohexylethyl methacrylate
4M-CHM-MA: 4-methylcyclohexylmethyl methacrylate
4M-CHMA: 4-methylcyclohexylmethyl acrylate
CHMA: cyclohexyl methacrylate
MMA: methyl methacrylate
St: styrene
BMA: butyl methacrylate
BA: n-butyl acrylate
2EHA: 2-ethylhexyl acrylate
AA: acrylic acid
HALS: 1,2,2,6,6-pentamethylpiperidinyl methacrylate
RUVA-93: 2-(2'-hydroxy-5-methacryloylethylphenyl)-2H-benzotriazole The resin compositions (1) to (8), as obtained in Examples 1 to 8 above, and the comparative resin compositions (1) to (3), as obtained in Comparative Examples 1 to 3 above, were evaluated by the weather resistance and the bending resistance (flexibility) as coating film properties. The results of these evaluations are shown in Tables 3 and 4.

Incidentally, the method and standard for evaluating the weather resistance and the bending resistance (flexibility) are as follows:

(Weather Resistance Test):

A white paint was prepared in the total quantity of 286.6 parts by mixing 146.7 parts of each of the resin compositions (1) to (8) and the comparative resin compositions (1) to (3) with 12.0 parts of a 75% aqueous butyl cellosolve solution, 64.6 parts of deionized water, 2.0 parts of Demol EP (produced by Kao Corporation), 60.0 parts of titanium oxide (rutile type), 0.3 part of NOPCO 8034 (produced by SAN NOPCO LIMITED), and 1.0 part of Adekanol UH-420 (produced by Asahi Denka Co., Ltd.). The resultant white paint was spray-coated onto a slate plate so as to form a dry film of 80 $\mu$m in thickness, and then the resultant film was dried in a hot-air drying oven of 80° C. for 10 minutes, thus obtaining a test plate.

An accelerated weathering test of this test plate was carried out with a sunshine weatherometer (Model No. WEL-SUN-HCB, produced by Suga Testing Machine Co., Ltd.). After 2,000 hours, the surface state of the test plate was observed by the eye to make judgment and evaluation on the following standard.

⊚: None of hazing, blistering, and cracking is observed.

○: A little hazing is observed, but neither blistering nor cracking is observed.

Δ: Hazing, blistering, and cracking are observed.

×: Hazing, blistering, and cracking are much observed.

(Bending Resistance Test: Evaluation of Flexibility of Formed Film):

This test was carried out in accordance with the JIS K5400 8.1 testing method for the resistance of a coating film.

Specimens were prepared by adding a 75% aqueous butyl cellosolve solution to each of the resin compositions (1) to (8) and the comparative resin compositions (1) to (3) so that the minimum film formation temperature (MFT) would be in the range of 0 to 10° C.

Each of the above specimens was coated onto an aluminum plate by using an applicator of 0.2 mm, and then left alone for 10 minutes, and then dried in a hot-air drying oven of 80° C. for 5 minutes, thus obtaining a test plate.

This test plate was aged at a test temperature in a temperature-controllable box along with a tester for not shorter than 2 hours, thus controlling the temperature. Then, the test was carried out at intervals of 5° C. under bending conditions where the diameter of the axle was 10 mm, thereby examining a temperature at which the coating film began cracking when the test plate was bent, and making evaluation based on a value of A in the following calculation equation:

(Temperature at which cracking occurred in the bending test)−(MFT)=A is calculated.

⊚: $-15°$ C. $\geq A$

○: $-10°$ C. $\geq A > -15°$ C.

Δ: $-5°$ C. $\geq A > 10°$ C.

×: $A > -5°$ C.

TABLE 1

|  | Example 1 | Example 2 | Example 3 | Example 4 | Example 5 | Example 6 | Example 7 | Example 8 |
|---|---|---|---|---|---|---|---|---|
| CHM-MA |  | 50 |  |  | 8 |  |  |  |
| CHE-MA |  |  |  |  | 22 | 40 |  |  |
| 4M-CHM-MA | 50 |  | 7 | 20 |  |  |  | 45 |
| 4M-CHMA |  |  |  |  |  |  | 40 |  |
| CHMA |  |  | 22 | 10 |  |  |  |  |
| MMA | 21 | 12 | 35 | 25 | 35 | 31 | 25 | 26 |
| St |  |  |  | 10 |  |  |  |  |
| BMA |  | 9 |  |  |  |  | 6 |  |
| BA |  |  | 15 | 10 |  |  |  |  |
| 2EHA | 28 | 28 | 20 | 24 | 34 | 28 | 27 | 27 |
| AA | 1 | 1 | 1 | 1 | 1 | 1 | 1 | 1 |
| HALS |  |  |  |  |  |  | 1 |  |
| RUVA-93 |  |  |  |  |  |  |  | 1 |

TABLE 2

|  | Comparative Example 1 | Comparative Example 2 | Comparative Example 3 |
|---|---|---|---|
| CHM-MA |  |  |  |
| CHE-MA |  |  |  |
| 4M-CHM-MA |  |  |  |
| 4M-CHMA |  |  |  |
| CHMA | 50 |  | 25 |
| MMA |  | 40 | 30 |
| St |  | 10 |  |
| BMA | 21 | 9 | 9 |
| BA |  | 12 | 15 |
| 2EHA | 28 | 28 | 20 |
| AA | 1 | 1 | 1 |
| HALS |  |  |  |
| RUVA-93 |  |  |  |

TABLE 3

|  | Example 1 | Example 2 | Example 3 | Example 4 | Example 5 | Example 6 | Example 7 | Example 8 |
|---|---|---|---|---|---|---|---|---|
| Nonvolatile content (wt %) | 45.0 | 44.7 | 44.8 | 45.1 | 44.9 | 44.8 | 45.0 | 44.7 |
| Viscosity (mPa·s) | 210 | 150 | 230 | 140 | 180 | 260 | 130 | 200 |
| pH | 8.6 | 8.7 | 8.7 | 8.6 | 8.6 | 8.6 | 8.6 | 8.6 |
| MFT (° C.) | 22 | 21 | 32 | 28 | 20 | 32 | 33 | 28 |
| Volume-average particle diameter (nm) | 148 | 150 | 140 | 160 | 150 | 142 | 153 | 145 |
| Calculated Tg (° C.) | 5 | 5 | 12 | 9 | 6 | 12 | 12 | 8 |
| Weather resistance | ⊙ | ⊙ | ○ | ○ | ⊙ | ⊙ | ⊙ | ⊙ |
| Bending resistance (flexibility) | ⊙ | ⊙ | ○ | ⊙ | ⊙ | ⊙ | ○ | ⊙ |

TABLE 4

|  | Comparative Example 1 | Comparative Example 2 | Comparative Example 3 |
|---|---|---|---|
| Nonvolatile content (wt %) | 44.8 | 44.6 | 44.8 |
| Viscosity (mPa.s) | 220 | 160 | 230 |
| pH | 8.6 | 8.7 | 8.7 |
| MFT (° C.) | 21 | 18 | 28 |
| Volume-average particle diameter (nm) | 145 | 152 | 140 |
| Calculated Tg (° C.) | 5 | 5 | 9 |
| Weather resistance | ⊙ | X | ⊙ |
| Bending resistance (flexibility) | X | ⊙ | Δ |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A (meth)acrylate ester-based resin composition, which comprises a (meth)acrylate ester-based polymer and an aqueous medium, wherein the (meth)acrylate ester-based polymer is obtained by a process including the step of polymerizing a monomer component including a polymerizable unsaturated monomer as an essential component wherein the polymerizable unsaturated monomer is a cyclohexylalkyl ester of (meth)acrylic acid wherein the cyclohexyl group may have a substituent, wherein said cyclohexyl group is separated from the acid group in the monomer by an alkylene group, and wherein the (meth)acrylate ester-based polymer is dispersed in the aqueous medium.

2. A (meth)acrylate ester-based resin composition according to claim 1, wherein the cyclohexylalkyl ester of (meth)acrylic acid is denoted by the following general formula (1):

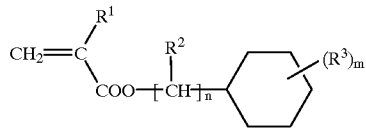

(1)

wherein: $R^1$ is a hydrogen atom or methyl group;

$R^2$ is a hydrogen atom or organic residue;

$R^3$ is an organic residue on the cyclohexyl group;

m is an integer of 0 to 2; and n is an integer of 1 to 4.

3. A (meth)acrylate ester-based resin composition according to claim 1, wherein the monomer component includes the cyclohexylalkyl ester of (meth)acrylic acid in a ratio of not less than 5 weight % to the monomer component.

4. A (meth)acrylate ester-based resin composition according to claim 1, which comprises the (meth)acrylate ester-based polymer in a ratio of 5–90 weight % to the (meth)acrylate ester-based resin composition.

5. A (meth)acrylate ester-based resin composition according to claim 1, which further comprises a pigment.

6. A (meth)acrylate ester-based polymer, which is obtained by a process including the step of polymerizing a monomer component including a polymerizable unsaturated monomer as an essential component wherein the polymerizable unsaturated monomer is a cyclohexylalkyl ester of (meth)acrylic acid wherein the cyclohexylalkyl ester of (meth)acrylic acid is denoted by the following general formula (2):

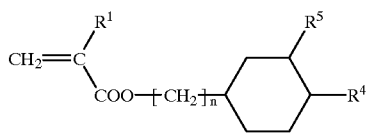

(2)

wherein: $R^1$ is a hydrogen atom or methyl group;

each of $R^4$ and $R^5$ is a hydrogen atom or organic residue wherein the case where $R^4$ and $R^5$ are simultaneously hydrogen atoms is excluded; and n is an integer of 1 to 4.

7. A (meth)acrylate ester-based polymer, which has a number-average molecular weight of 1,000 to 20,000,000 and a structural unit that is derived from a cyclohexylalkyl ester of (meth)acrylic acid and denoted by the following general formula (3):

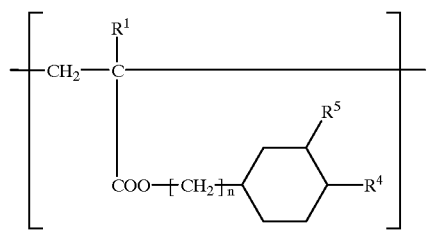

(3)

wherein: $R^1$ is a hydrogen atom or methyl group;

each of $R^4$ and $R^5$ is a hydrogen atom or organic residue wherein the case where $R^4$ and $R^5$ are simultaneously hydrogen atoms is excluded; and n is an integer of 1 to 4.

8. A cyclohexylalkyl ester of (meth)acrylic acid, which is denoted by the following general formula (2):

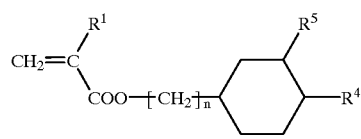

(2)

wherein: $R^1$ is a hydrogen atom or methyl group;

each of $R^4$ and $R^5$ is a hydrogen atom or organic residue wherein the case where $R^4$ and $R^5$ are simultaneously hydrogen atoms is excluded; and n is an integer of 1 to 4.

* * * * *